United States Patent
Dodge

(10) Patent No.: US 6,802,822 B1
(45) Date of Patent: Oct. 12, 2004

(54) DISPENSER FOR AN ADHESIVE TISSUE SEALANT HAVING A FLEXIBLE LINK

(75) Inventor: Larry H. Dodge, River Falls, WI (US)

(73) Assignee: 3M Innovative Properties Company, St. Paul, MN (US)

(*) Notice: Subject to any disclaimer, the term of this patent is extended or adjusted under 35 U.S.C. 154(b) by 416 days.

(21) Appl. No.: 09/540,592

(22) Filed: Mar. 31, 2000

(51) Int. Cl.⁷ .................................................. A61B 17/03
(52) U.S. Cl. .................................. 604/82; 606/213
(58) Field of Search ............................ 606/213, 214, 606/215; 604/82, 83, 84, 85

(56) References Cited

U.S. PATENT DOCUMENTS

| | | | | |
|---|---|---|---|---|
| 3,223,083 A | * | 12/1965 | Cobey | 524/460 |
| 4,359,049 A | * | 11/1982 | Redl et al. | 604/191 |
| 4,735,616 A | | 4/1988 | Eibl et al. | |
| 5,004,128 A | * | 4/1991 | Richichi et al. | 222/325 |
| 5,242,449 A | | 9/1993 | Zaleski | 606/107 |
| 5,583,114 A | | 12/1996 | Barrows et al. | 514/21 |
| 5,620,447 A | * | 4/1997 | Smith et al. | 604/22 |
| 5,722,829 A | * | 3/1998 | Wilcox et al. | 222/137 |
| 5,814,066 A | | 9/1998 | Spotnitz | 606/214 |
| 5,842,973 A | * | 12/1998 | Bullard | 600/114 |
| 5,938,439 A | * | 8/1999 | Mertins et al. | 433/90 |

FOREIGN PATENT DOCUMENTS

| | | |
|---|---|---|
| EP | 0 858 775 A1 | 8/1998 |
| FR | 2 722 104 | 1/1996 |
| WO | WO 97/28834 | 8/1997 |
| WO | WO 98/42260 | 10/1998 |
| WO | WO99/56634 | 11/1999 |

* cited by examiner

*Primary Examiner*—Edward K. Look
*Assistant Examiner*—Richard A Edgar
(74) *Attorney, Agent, or Firm*—John A. Burtis; Daniel R. Pastirik

(57) ABSTRACT

A dispensing tip for e.g. a syringe dispensing an adhesive tissue sealant, having two rigid sections connected together by a flexible section. Preferably, although bendable, the flexible section has enough resilience that in the absence of external force the two rigid sections are held at a predictable angle to one another. In this way manual dispensing into hard to reach places during surgery is facilitated. This flexibility also facilitates use of the dispensing tip with a cannula.

4 Claims, 2 Drawing Sheets

DISPENSER FOR AN ADHESIVE TISSUE SEALANT HAVING A FLEXIBLE LINK

TECHNICAL FIELD

The invention relates generally to the dispensing of adhesive tissue sealants and other liquid preparations, including those requiring mixing immediately prior to use.

BACKGROUND OF THE INVENTION

A variety of techniques have been used to bond or seal living tissue. For example, different types of tissues have been mechanically bound or sealed with a number of procedures, materials and methods including sutures, staples, tapes and bandages. In some applications, these materials are made of absorbable materials that are intended to bond and/or seal tissue as it heals and then to be absorbed over a period of time.

A recent addition to the techniques that can be used is application of an absorbable adhesive sealant composition to bond and/or seal tissue. The adhesive composition is readily formed from a two component mixture that includes a first part of a cross-linking agent and a second part of a protein, preferably a serum protein such as albumin. When the two parts of the mixture are combined, the mixture is initially liquid. The combined mixture then cures in vivo on the surface of tissue to give a substantive composition that securely bonds to the tissue. A more complete discussion can be found in coassigned U.S. Pat. No. 5,583,114, "ADHESIVE SEALANT COMPOSITION," to Barrows et al, the entire contents of which are hereby incorporated by reference.

This material is most conveniently dispensed from a dual syringe which maintains the two parts strictly separate until just before they are dispensed onto the tissue because the reaction time to the forming of the finished sealant is quite fast. Copending and coassigned U.S. application Ser. No. 09/524,141, filed Mar. 10, 2000, Wirt et al., the entire contents of which are hereby incorporated by reference, discloses a particularly suitable dual syringe that uses twin carpules to contain the liquid components. When the user presses on the pistons the liquid components are pressurized into flow passageways and into a dispensing tip. The nozzle of the dual syringe and the structure of the dispensing tip keep the two components separate until the proper time for mixing.

A limitation that remains on the use of this sealant and its dispenser is the short, straight dispensing tip is sometimes inadequate for working in the confined spaces of a surgical site. An angled tip would often be more suitable, but an angled tip could not be inserted into the long, narrow cannulas which are often used these days to access body organs with minimum incisions.

SUMMARY OF THE INVENTION

The present invention provides a dispensing tip having two rigid sections connected together by a flexible section. Preferably, although bendable, the flexible section has enough resilience that in the absence of external force the two rigid sections are held at a predictable angle to one another. In this way manual dispensing into hard to reach places during surgery is facilitated. However, if it is suddenly decided that the dispensing through a cannula into a largely closed body cavity is desired, a flip of the wrist straightens the distal rigid section enough to allow the dispensing tip to be inserted into the straight cannula. When the distal rigid section emerges from the far end of the cannula inside the patient's body, it resiliently returns to its convenient angled orientation.

More specifically, the dispensing tip has a first rigid section having at least one lumen passing therethough. Preferred embodiments, particularly for the composition of U.S. Pat. No. 5,583,114, have two lumens that keep the components of the composition separate throughout substantially all of the length of the first rigid section. The dispensing tip also has a flexible section attached to the first rigid section. Distal to the flexible section is a second rigid section attached to the flexible section. This second rigid section has an opening for dispensing material conducted through the lumen. Preferred embodiments include a static mixer within at least a portion of the second rigid section that the components encounter before reaching the opening. A static mixing element may optionally appear within the flexible section, depending on the length chosen for the second rigid section, and depending on how much mixing the solution being dispensed requires.

In preferred embodiments, the dispensing tip is such that the flexible section has a preset bend so as to urge the first and the second rigid sections towards a preset angle to one another. For many surgical purposes, an angle of between about 20 and 45 degrees will suit the surgeon's need best. In particular, an angle of about 30 degrees is considered particularly desirable. However, for some specialized purposes, particularly in surgery to repair a pneumothorax, a much sharper bend, even as much as 180 degrees will occasionally be useful to e.g. spray the adhesive sealant on a hard-to-reach point on the backside of the lung.

Other features and advantages of the invention will be apparent from the following description and drawings, and from the claims.

DETAILED DESCRIPTION

Figure 1:
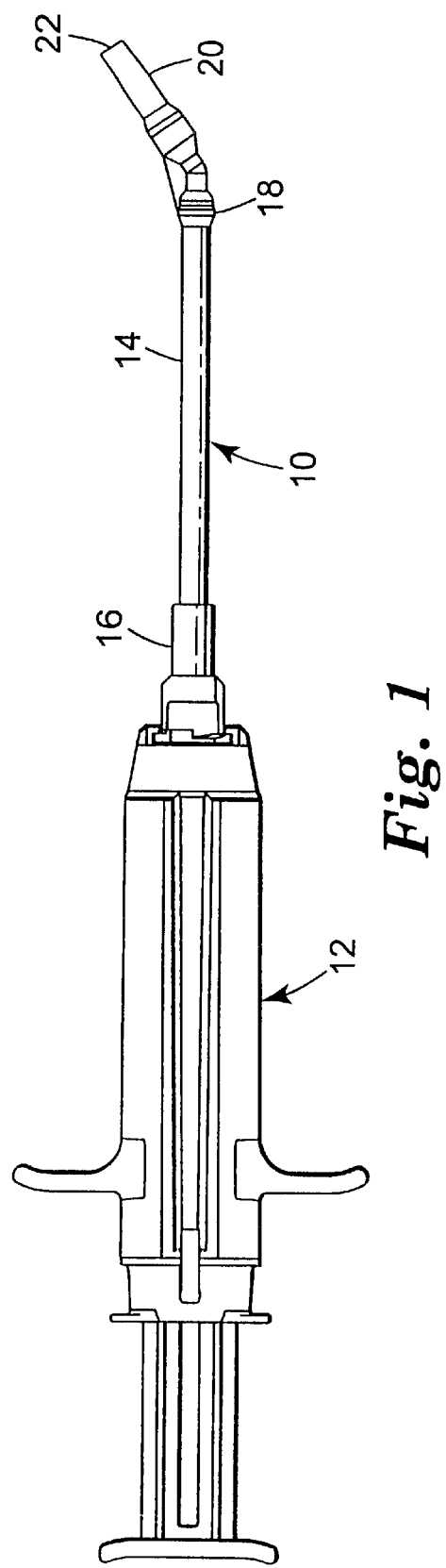
FIG. 1 is a plan view of a preferred embodiment of the dispensing tip of the invention, illustrated attached to a representative dual syringe.

Referring now to FIG. 1, a plan view of a preferred embodiment of the dispensing tip 10 of the invention is illustrated. For convenience in understanding its complete function, it is illustrated attached to a representative dual syringe 12. A dual syringe generally as described in copending and coassigned U.S. application Ser. No. 09/524,141, filed Mar. 10, 2000, Wirt et al., incorporated by reference above, is shown for illustration purposes, but it will be understood that the dispensing tip has more general applicability to other similar dispensers.

The dispensing tip 10 includes a first rigid section 14, which in most preferred embodiments includes an attachment portion 16 adapted to engage the dispensing tip with the nozzle of the syringe to other fluid dispensing device it is intended to work with. A flexible section 18 is attached to the first rigid section 14, and this flexible section in turn is attached to a second rigid section 20. The second rigid section 20 has an opening 22 where the components in the syringe 12, e.g. an adhesive surgical sealant, are ejected.

Figure 2:
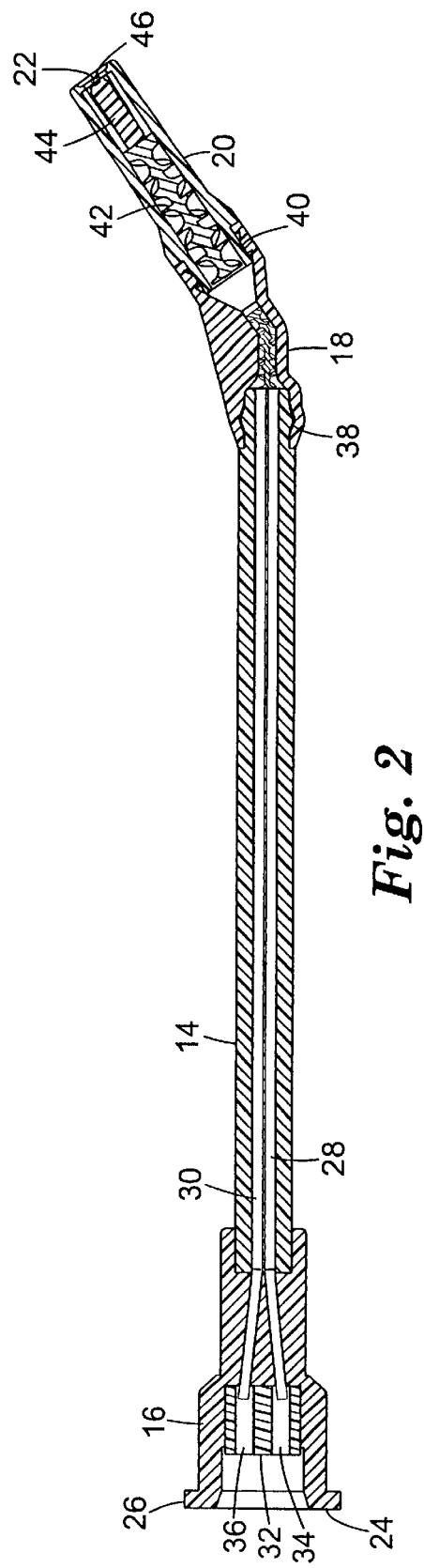
FIG. 2 is a cross section plan view of the dispensing tip of FIG. 1 in isolation.

Referring now to FIG. 2, a cross section plan view of the dispensing tip of FIG. 1 is illustrated in isolation. In this view it can be more readily seen that the attachment portion 16 conveniently has flanges 24 and 26 to facilitate attachment, of the dispensing tip 10 to the syringe with which it is to be used. The first rigid section 14 has two passageways 28 and 30. It will be observed that these passageway maintain the components that they carry from the syringe towards the opening 22 separate at least until the flexible section 18 is reached. This is not a requirement of the invention, but is frequently preferred with many of the known tissue sealants and glues. A seal element 32, having through holes 34 and 36 that communicate with passageways 28 and 30, is used to make a liquid tight seal between the exit holes on the nozzle of the syringe and the passageways.

The flexible section 18 is conveniently attached to the first and second rigid sections 14 and 20 by barbs 38 and 40 respectively. When a simple barb connection is made, the user of the dispenser may rotate the second rigid section 20 about the axis of the first rigid section 14 to whatever orientation is most convenient. Depending on material choices and the forces that need to be resisted, the use of adhesive bonding, solvent welding, sonic welding or clinch rings might also be suitable. Other mechanical expedients will suggest themselves to the artisan.

If the components being ejected from the syringe require it, a static mixing element 42 is conveniently placed within the second rigid section 20. If even further mixing is desirable, the partially mixed components may be conducted around pathways alongside a break-up piece 44 to e.g. a swirl chamber 46 adjacent the opening 22.

The seal member 32 and the flexible section 18 are conveniently made from a medical grade silicone, but they can be fabricated from any rubber-like material that is biologically acceptable. The first and second rigid sections 14 and 20 are conveniently fabricated by injection molding of a polymer. A medical grade polycarbonate is presently considered preferred. It is presently considered preferred that the outside diameter of the elongated part of the first rigid section 14, and second rigid section 20, and the flexible section 18 be no more than about 7 mm in size so that after the flexible section is bent for insertion, the whole can enter an 8 mm cannula.

What is claimed is:

1. A dispensing tip, comprising:
   (a) a first rigid section having at least one lumen therethrough;
   (b) a flexible section attached to the first rigid section; and
   (c) a second rigid section attached to the flexible section, the second rigid section having an opening for dispensing material conducted through the lumen;
   wherein the first rigid section has at least two lumens therethrough, wherein the second rigid element further comprises at least one static mixing element for mixing material conducted through the lumens prior to reaching the opening, and wherein the flexible section has a preset bend so as to urge the first and the second rigid sections towards a preset angle to one another.

2. The dispensing tip according to claim 1 wherein the preset angle is between about 20 and 45 degrees.

3. The dispensing tip according to claim 2 wherein the preset angle is about 30 degrees.

4. The dispensing tip according to claim 1 wherein the first rigid section is adapted to engage a dual syringe having at least two exit ports such that liquids dispensed from the exit ports each enter a different one of the lumens and are kept separate within the first rigid section.

* * * * *

UNITED STATES PATENT AND TRADEMARK OFFICE
CERTIFICATE OF CORRECTION

PATENT NO.    : 6,802,822 B1
DATED         : October 12, 2004
INVENTOR(S)   : Dodge, Larry H.

It is certified that error appears in the above-identified patent and that said Letters Patent is hereby corrected as shown below:

Column 2,
Line 67, after "tip" insert -- 10 --;

Column 3,
Line 3, delete "," before "of".

Signed and Sealed this

Twenty-fourth Day of January, 2006

JON W. DUDAS
*Director of the United States Patent and Trademark Office*